(12) United States Patent
Waddell et al.

(10) Patent No.: US 7,981,910 B2
(45) Date of Patent: Jul. 19, 2011

(54) TRIAZOLE DERIVATIVES AS INHIBITORS OF 11-β-HYDROXYSTEROID DEHYDROGENASE-1

(75) Inventors: Sherman T. Waddell, Westfield, NJ (US); James M. Balkovec, Martinsville, NJ (US); Nancy J. Kevin, East Brunswick, NJ (US); Xin Gu, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 368 days.

(21) Appl. No.: 12/083,047

(22) PCT Filed: Oct. 16, 2006

(86) PCT No.: PCT/US2006/040459
§ 371 (c)(1),
(2), (4) Date: Apr. 3, 2008

(87) PCT Pub. No.: WO2007/047625
PCT Pub. Date: Apr. 26, 2007

(65) Prior Publication Data
US 2009/0258913 A1    Oct. 15, 2009

Related U.S. Application Data

(60) Provisional application No. 60/728,723, filed on Oct. 20, 2005.

(51) Int. Cl.
*A61K 31/4245* (2006.01)
*C07D 271/06* (2006.01)
*C07D 271/10* (2006.01)

(52) U.S. Cl. ......... 514/364; 548/131; 548/143; 548/145
(58) Field of Classification Search ............... None
See application file for complete search history.

(56) References Cited

U.S. PATENT DOCUMENTS

| | | | |
|---|---|---|---|
| 6,849,636 B2 * | 2/2005 | Waddell et al. | 514/256 |
| 2004/0133011 A1 * | 7/2004 | Waddell et al. | 548/266.2 |

OTHER PUBLICATIONS

Morissette et al. "High-throughput crystallization: polymorphs, salts, co-crystals and solvates of pharmaceutical solids." Advanced Drug Delivery Reviews 2004, 56, 275-300.*
Patani et al., Chem Rev., 1996, 96, 3147-76.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
Gu, et al., Bioorganic & Medicinal Chemistry Letters, vol. 15(23), pp. 5266-5269 (2005).
Seckl, et al., Endocrinology, vol. 142, No. 4, pp. 1371-1376 (2001).

* cited by examiner

*Primary Examiner* — Yong Chu
*Assistant Examiner* — Alicia L Otton
(74) *Attorney, Agent, or Firm* — Matthew A. Leff; Heidi M. Struse; Richard S. Parr

(57) ABSTRACT

Triazole derivatives of structural formula I are selective inhibitors of the 11β-hydroxysteroid dehydrogenase-1. The compounds are useful for the treatment of diabetes, such as noninsulin-dependent diabetes (NIDDM), hyperglycemia, obesity, insulin resistance, dyslipidemia, hyperlipidemia, hypertension, Metabolic Syndrome, and other symptoms associated with NIDDM.

10 Claims, No Drawings

TRIAZOLE DERIVATIVES AS INHIBITORS OF 11-β-HYDROXYSTEROID DEHYDROGENASE-1

PRIORITY CLAIM

This application is a §371 application of PCT/US06/040459 that was filed on Oct. 16, 2006, which claims priority from the U.S. Provisional Application No. 60/728,723, filed on Oct. 20, 2005, now expired.

FIELD OF THE INVENTION

The present invention relates to triazole derivatives as inhibitors of the enzyme 11-beta-hydroxysteroid dehydrogenase Type I (11β-HSD1 or HSD1) and methods of treating certain conditions using such compounds. The compounds of the present invention are useful for the treatment of diabetes, such as non-insulin dependent Type 2 diabetes mellitus (NIDDM), insulin resistance, obesity, lipid disorders, hypertension, cognition, increased intraocular pressure, the facilitation of wound healing and other diseases and conditions.

BACKGROUND OF THE INVENTION

Diabetes is caused by multiple factors and is most simply characterized by elevated levels of plasma glucose (hyperglycemia) in the fasting state. There are two generally recognized forms of diabetes: Type 1 diabetes, or insulin-dependent diabetes mellitus (IDDM), in which patients produce little or no insulin, the hormone which regulates glucose utilization, and Type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, Type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Type 2 diabetics are at increased risk of developing cardiovascular complications, e.g., atherosclerosis, coronary heart disease, stroke, peripheral vascular disease, hypertension, nephropathy, neuropathy and retinopathy. Therefore, therapeutic control of glucose homeostasis, lipid metabolism, obesity and hypertension are critically important in the clinical management and treatment of diabetes mellitus.

Many patients who have insulin resistance but have not developed Type 2 diabetes are also at a risk of developing symptoms referred to as "Syndrome X" or "Metabolic Syndrome". Syndrome X or Metabolic Syndrome is characterized by insulin resistance, along with abdominal obesity, hyperinsulinemia, high blood pressure, low HDL and high VLDL. These patients, whether or not they develop overt diabetes mellitus, are at increased risk of developing the cardiovascular complications listed above.

There is a continuing need for new methods of treating diabetes and related conditions, such as Metabolic Syndrome. The present invention meets this and other needs.

SUMMARY OF THE INVENTION

The present invention addresses a compound represented by formula I:

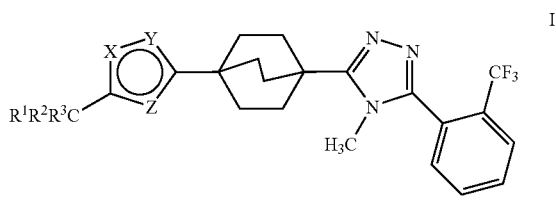

or a pharmaceutically acceptable salt or solvate thereof wherein:
2 of X, Y and Z represent nitrogen atoms, and the other represents an oxygen atom;
$R^1$ and $R^2$ are taken together with the atom to which they are attached and represent a cyclobutyl group, optionally substituted with 1-2 fluorine atoms, and $R^3$ represents hydrogen or a fluorine atom;
or $R^1$ represents methyl,
$R^2$ represents methyl or a fluorine atom and
$R^3$ represents a fluorine atom.

DETAILED DESCRIPTION OF THE INVENTION

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

These bicyclo[2.2.2]octyltriazole derivatives are effective as inhibitors of 11-hydroxysteroid dehydrogenase type 1 (11β-HSD1). They are therefore useful for the treatment, control or prevention of disorders responsive to the inhibition of 11β-HSD1, such as Type 2 diabetes, lipid disorders, obesity, atherosclerosis, cognition enhancement, such as is required for the treatment of Alzheimer's disease and related conditions, hypertension, increased intraocular pressure, the facilitation of wound healing, and Metabolic Syndrome.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of 11β-HSD1 in a subject in need thereof by administering the compounds and pharmaceutical compositions of the present invention.

The present invention also relates to methods for the treatment or control of Type 2 diabetes, obesity, lipid disorders, atherosclerosis, and Metabolic Syndrome by administering the compounds and pharmaceutical compositions of the present invention.

The present invention also relates to methods for treating obesity by administering the compounds of the present invention in combination with a therapeutically effective amount of another agent known to be useful to treat the condition.

The present invention also relates to methods for treating Type 2 diabetes by administering the compounds of the present invention in combination with a therapeutically effective amount of another agent known to be useful to treat the condition.

The present invention also relates to methods for treating atherosclerosis by administering the compounds of the present invention in combination with a therapeutically effective amount of another agent known to be useful to treat the condition.

The present invention also relates to methods for treating lipid disorders by administering the compounds of the present invention in combination with a therapeutically effective amount of another agent known to be useful to treat the condition.

The present invention also relates to methods for treating Metabolic Syndrome by administering the compounds of the present invention in combination with a therapeutically effective amount of another agent known to be useful to treat the condition.

The present invention is also concerned with the use of the compounds of structural formula I for the treatment hyperglycemia, insulin resistance, Type 2 diabetes, lipid disorders, obesity, atherosclerosis, and Metabolic Syndrome The present invention also provides for the use of the compounds of structural formula I in the manufacture of a medicament for use in the treatment of hyperglycemia, insulin resistance, Type 2 diabetes, lipid disorders, obesity, atherosclerosis, and Metabolic Syndrome.

The present invention also relates to methods for treating hypertension by administering a compound of the present invention in an amount that is effective to treat hypertension. Such treatment can involve monotherapy with a compound of formula I, or multiple drug therapy wherein the compound of formula I is administered in an amount that is effective to treat hypertension in combination with a therapeutically effective amount of another agent known to be useful to treat the condition.

The present invention also relates to a method for enhancing cognition, comprising administering a compound of the present invention in an amount that is effective to enhance cognition. Such treatment can involve monotherapy with a compound of formula I, or multiple drug therapy wherein the compound of formula I is administered in an amount that is effective to enhance cognition in combination with a therapeutically effective amount of another agent known to be useful to treat the condition.

The present invention also relates to methods for treating Alzheimer's disease by administering a compound of the present invention in an amount that is effective to treat Alzheimer's disease. Such treatment can involve monotherapy with a compound of formula I, or multiple drug therapy wherein the compound of formula I is administered in an amount that is effective to treat Alzheimer's disease in combination with a therapeutically effective amount of another agent known to be useful to treat the condition.

The present invention also relates to methods for improving wound healing, by administering a compound of the present invention in an amount that is effective to improve wound healing. Such treatment can involve monotherapy with a compound of formula I, or multiple drug therapy wherein the compound of formula I is administered in an amount that is effective to promote wound healing in combination with a therapeutically effective amount of another agent known to be useful to treat the condition.

The present invention also relates to methods for lowering intraocular pressure by administering a compound of the present invention in an amount that is effective to lower intraocular pressure. Such treatment can involve monotherapy with a compound of formula I, or multiple drug therapy wherein the compound of formula I is administered in an amount that is effective to lower intraocular pressure in combination with a therapeutically effective amount of another agent known to be useful to treat the condition.

The present invention also relates to methods for treating glaucoma by administering a compound of the present invention in an amount that is effective to treat glaucoma. Such treatment can involve monotherapy with a compound of formula I, or multiple drug therapy wherein the compound of formula I is administered in an amount that is effective to treat glaucoma in combination with a therapeutically effective amount of another agent known to be useful to treat the condition.

In a different aspect of the invention, a pharmaceutical composition is addressed comprising a compound in accordance with structural formula I, or a pharmaceutically acceptable salt or solvate thereof, in combination with a pharmaceutically acceptable carrier. By the term "solvate" is meant a hydrate, an alcoholate, or other solvate of crystallization.

In another aspect of the invention, a method of treating a lipid disorder selected from the group consisting of dyslipidemia, hyperlipidemia, hypertriglyceridemia, hypercholesterolemia, low HDL, and high LDL in a mammalian patient in need of such treatment is disclosed, comprising administering to said patient a compound in accordance with structural formula I in an amount that is effective to treat said lipid disorder.

In another aspect of the invention, a method of treating atherosclerosis in a mammalian patient in need of such treatment is disclosed, comprising administering to said patient a compound in accordance with structural formula I in an amount effective to treat atherosclerosis.

In another aspect of the invention, a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension, (22) Alzheimer's disease, (23) glaucoma, (24) slow or poor wound healing and other conditions and disorders where insulin resistance is a component, in a mammalian patient in need of such treatment is disclosed, comprising administering to the patient a compound in accordance with structural formula I in an amount that is effective to treat said condition.

In another aspect of the invention, a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component in a mammalian patient in need of such treatment is disclosed, comprising administering to the patient a compound in accordance with structural formula I in an amount that is effective to delay the onset of said condition.

In another aspect of the invention, a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component in a mammalian patient in need of such treatment is disclosed, comprising administering to the patient a compound in accordance with structural formula I in an amount that is effective to reduce the risk of developing said condition.

In another aspect of the invention, a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component, in a mammalian patient in need of such treatment, comprising administering to the patient an effective amount of a compound as defined in structural formula I and a compound selected from the group consisting of:

(a) dipeptidyl peptidase-IV (DPP-IV) inhibitors;
(b) insulin sensitizing agents selected from the group consisting of (i) PPAR alpha agonists, (ii) PPAR gamma agonists, (iii) PPAR alpha/gamma dual agonists, and (iv) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 analogs, and GLP-1 receptor agonists;
(h) GIP, GIP mimetics, and GIP receptor agonists;
(i) PACAP, PACAP mimetics, and PACAP receptor 3 agonists;
(j) cholesterol lowering agents selected from the group consisting of
(i) HMG-CoA reductase inhibitors, (ii) sequestrants, (iii) nicotinyl alcohol, nicotinic acid and salts thereof, (iv) inhibitors of cholesterol absorption, (v) acyl CoA:cholesterol acyltransferase inhibitors, and (vi) anti-oxidants;
(k) PPAR delta agonists;
(l) antiobesity compounds;
(m) ileal bile acid transporter inhibitors;
(n) anti-inflammatory agents, excluding glucocorticoids;
(o) protein tyrosine phosphatase 1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; said compounds being administered to the patient in an amount that is effective to treat said condition.

Dipeptidyl peptidase-W inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001)

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB 1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists, *Expert Opin. Ther. Patents*, 12: 1631-1638 (2002).

In another aspect of the invention, a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment is disclosed, comprising administering to the patient a therapeutically effective amount of a compound as defined in structural formula I and an HMG-CoA reductase inhibitor.

More particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin.

Even more particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin selected from the group consisting of lovastatin, simvastatin, pravastatin, cerivastatin, fluvastatin, atorvastatin, itavastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound as defined in structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound as defined in structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin.

Even more particularly, a method for delaying the onset or reducing the risk of developing atherosclerosis in a human patient in need of such treatment is disclosed, wherein the HMG-Co A reductase inhibitor is a statin selected from the group consisting of: lovastatin, simvastatin, pravastatin, cerivastatin, fluvastatin, atorvastatin, itavastatin, and rosuvastatin.

Even more particularly, a method for delaying the onset or reducing the risk of developing atherosclerosis in a human patient in need of such treatment is disclosed, wherein the statin is simvastatin.

In another aspect of the invention, a method for delaying the onset or reducing the risk of developing atherosclerosis in a human patient in need of such treatment is disclosed, wherein the HMG-CoA reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises
(1) a compound according to structural formula I,
(2) a compound selected from the group consisting of:
  (a) DP-IV inhibitors;
  (b) insulin sensitizing agents selected from the group consisting of (i) PPAR alpha agonists; (ii) PPAR gamma agonists, (iii) PPAR alpha/gamma dual agonists, and (iv) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 analogs, and GLP-1 receptor agonists;
  (h) GIP, GIP mimetics, and GIP receptor agonists;
  (i) PACAP, PACAP mimetics, and PACAP receptor 3 agonists;
  (j) cholesterol lowering agents selected from the group consisting of (i) HMG-CoA reductase inhibitors, (ii) sequestrants, (iii) nicotinyl alcohol, nicotinic acid or a salt thereof, (iv) inhibitors of cholesterol absorption, (v) acyl CoA:cholesterol acyltransferase inhibitors, and (vi) anti-oxidants;
  (k) PPAR delta agonists;
  (l) antiobesity compounds;
  (m) ileal bile acid transporter inhibitors;
  (n) anti-inflammatory agents other than glucocorticoids;
  (o) protein tyrosine phosphatase 1B (PTP-1B) inhibitors; and
  (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and
(3) a pharmaceutically acceptable carrier.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of structural formula I are included in the present invention as well.

The compounds described herein are selective inhibitors of the 11β-HSD1 enzyme. Thus, the present invention relates to the use of the 11β-HSD1 inhibitors for inhibiting the reductase activity of 11β-hydroxysteroid dehydrogenase, which is responsible for the conversion of cortisone to cortisol. Excess cortisol is associated with numerous disorders, including NIDDM, obesity, dyslipidemia, insulin resistance and hypertension. Administration of the compounds of the present invention decreases the level of cortisol and other 11β-hydroxysteroids in target tissues, thereby reducing the effects of excessive amounts of cortisol and other 11β-hydroxysteroids. Inhibition of 11β-HSD1 can be used to treat and control diseases mediated by abnormally high levels of cortisol and other 11β-hydroxysteroids, such as NIDDM, obesity, hypertension and dyslipidemia. Inhibition of 11β-HSD1 activity in the brain such as to lower cortisol levels may also be useful to treat or reduce anxiety, depression, and cognitive impairment.

The present invention includes the use of an 11β-HSD1 inhibitor for the treatment, control, amelioration, prevention, delaying the onset of or reducing the risk of developing the diseases and conditions that are described herein, as mediated by excess or uncontrolled amounts of cortisol and/or other corticosteroids in a mammalian patient, particularly a human, by the administration of an effective amount of a compound of structural formula I or a pharmaceutically acceptable salt or solvate thereof. Inhibition of the 11β-HSD1 enzyme limits the conversion of cortisone, which is normally inert, to cortisol, which can cause or contribute to the symptoms of these diseases and conditions if present in excessive amounts.

NIDDM and Hypertension:

The compounds of this invention are selective inhibitors of 11β-HSD1 over 11β-HSD2. While the inhibition of 11β-HSD1 is useful for reducing cortisol levels and treating conditions related thereto, inhibition of 11β-HSD2 is associated with serious side effects, such as hypertension.

Cortisol is an important and well recognized anti-inflammatory hormone, which also acts as an antagonist to the action of insulin in the liver, such that insulin sensitivity is reduced, resulting in increased gluconeogenesis and elevated levels of glucose in the liver. Patients who already have impaired glucose tolerance have a greater probability of developing Type 2 diabetes in the presence of abnormally high levels of cortisol.

High levels of cortisol in tissues where the mineralocorticoid receptor is present often lead to hypertension. Inhibition of 11β-HSD1 shifts the ratio of cortisol and cortisone in specific tissues in favor of cortisone.

Administration of a therapeutically effective amount of an 11β-HSD1 inhibitor is effective in treating, controlling and ameliorating the symptoms of NIDDM, and administration of a therapeutically effective amount of an 11β-HSD1 inhibitor on a regular basis delays or prevents the onset of NIDDM, particularly in humans.

Cushing's Syndrome:

The effect of elevated levels of cortisol is also observed in patients who have Cushing's Syndrome, which is a metabolic disease characterized by high levels of cortisol in the blood stream. Patients with Cushing's Syndrome often develop NIDDM.

Obesity, Metabolic Syndrome, Dyslipidemia:

Excessive levels of cortisol have been associated with obesity, perhaps due to increased hepatic gluconeogenesis. Abdominal obesity is closely associated with glucose intolerance, hyperinsulinemia, hypertriglyceridemia, and other factors of Metabolic Syndrome, such as high blood pressure, elevated VLDL and reduced HDL. Montague et al., *Diabetes,* 2000, 49: 883-888. Thus, the administration of an effective amount of an 11β-HSD1 inhibitor is useful in the treatment or control of obesity. Long-term treatment with an 11β-HSD1 inhibitor is also useful in delaying or preventing the onset of obesity, especially if the patient uses an 11β-HSD1 inhibitor in combination with controlled diet and exercise.

By reducing insulin resistance and maintaining serum glucose at normal concentrations, compounds of the present invention also have utility in the treatment and prevention of conditions that accompany Type II diabetes and insulin resistance, including the Metabolic Syndrome or Syndrome X, obesity, reactive hypoglycemia and diabetic dyslipidemia.

Cognition and Dementia:

Excessive levels of cortisol in the brain may also result in neuronal loss or dysfunction through the potentiation of neurotoxins. Cognitive impairment has been associated with aging, and excess levels of cortisol in the brain. See J. R. Seckl and B. R. Walker, *Endocrinology,* 2001, 142: 1371-1376, and references cited therein. Administration of an effective amount of an 11β-HSD1 inhibitor results in the reduction, amelioration, control or prevention of cognitive impairment associated with aging and of neuronal dysfunction. Inhibitors of 11β-HSD1 may also be useful to treat anxiety and depression.

Atherosclerosis:

As described above, inhibition of 11β-HSD1 activity and a reduction in the amount of cortisol are beneficial in treating or controlling hypertension. Since hypertension and dyslipidemia contribute to the development of atherosclerosis, administration of a therapeutically effective amount of an 11β-HSD1 inhibitor of the present invention may be especially beneficial in treating, controlling, delaying the onset of or preventing atherosclerosis.

Effects on Pancreas:

Inhibition of 11β-HSD1 activity in isolated murine pancreatic β-cells improves glucose stimulated insulin secretion (B. Davani et al., *J. Biol. Chem.,* 2000, 275: 34841-34844). Glucocorticoids have been shown to reduce insulin secretion in vivo. (B. Billaudel et al., *Horm. Metab. Res.,* 1979, 11: 555-560).

Reduction of Intraocular Pressure:

Recent data suggests a connection between the levels of glucocorticoid target receptors and the 11β-HSD enzymes and the susceptibility to glaucoma (J. Stokes et al., *Invest. Ophthamol.,* 2000, 41: 1629-1638). Therefore, inhibition of 11β-HSD1 activity is useful in reducing intraocular pressure in the treatment of glaucoma.

Immunomodulation:

In certain disease states, such as tuberculosis, psoriasis, and even under conditions of excessive stress, high glucocorticoid activity shifts the immune response to a humoral response, when in fact a cell based response may be more beneficial to the patient. Inhibition of 11β-HSD1 activity and the attendant reduction in glucocorticoid levels shifts the immune response toward a cell based response. See D. Mason, *Immunology Today,* 1991, 12: 57-60, and G. A. W. Rook, *Baillièr's Clin. Endocrinol. Metab.,* 1999, 13: 576-581.

Osteoporosis:

Glucocorticoids can inhibit bone formation, which can result in a net bone loss. 11β-HSD1 has a role in bone resorption. Inhibition of 11β-HSD1 is beneficial in preventing bone loss due to osteoporosis. See C. H. Kim et al., *J. Endocrinol.,* 1999, 162: 371-379; C. G. Bellows et al., *Bone,* 1998, 23: 119-125; and M. S. Cooper et al., *Bone,* 2000, 27: 375-381.

Other Utilities:

The following diseases, disorders and conditions can be treated, controlled, prevented or delayed, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other disorders where insulin resistance is a component.

The above diseases and conditions can be treated using the compounds of structural formula I, or the compound can be administered to prevent or reduce the risk of developing the diseases and conditions described herein. Since concurrent inhibition of 11β-HSD2 may have deleterious side effects or may actually increase the amount of cortisol in the target tissue where reduction of cortisol is desired, selective inhibitors of 11β-HSD1 with little or no inhibition of 11β-HSD2 are desirable.

The 11β-HSD1 inhibitors of structural formula I generally have an inhibition constant $IC_{50}$ of less than about 500 nM, and preferably less than about 100 nM. Generally, the $IC_{50}$ ratio for 11β-HSD2 to 11β-HSD1 of a compound is at least about two or more, and preferably about ten or greater. Even more preferred are compounds with an $IC_{50}$ ratio for 11β-HSD2 to 11β-HSD1 of about 100 or greater. For example, compounds of the present invention ideally demonstrate an inhibition constant $IC_{50}$ against 11β-HSD2 greater than about 1000 nM, and preferably greater than 4000 nM.

Compounds of structural formula I may be used in combination with one or more other drugs in the treatment, prevention, suppression or amelioration of diseases or conditions for which compounds of structural formula I or the other drugs have utility. Typically the combination of the drugs is safer or more effective than either drug alone, or the combination is safer or more effective than would be expected based on the additive properties of the individual drugs. Such other drug(s) may be administered, by a route and in an amount commonly used contemporaneously or sequentially with a compound of structural formula I. When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I.

Examples of other active ingredients that may be administered in combination with a compound of structural formula I, and either administered separately or in the same pharmaceutical composition, include, but are not limited to:

(a) dipeptidyl peptidase IV (DPP-IV) inhibitors;

(b) insulin sensitizing agents including (i) PPAR delta agonists such as the glitazones (e.g. troglitazone, pioglitazone, englitazone, MCC-555, rosiglitazone, and the like) and other PPAR ligands, including PPAR alpha/gamma dual agonists, such as KRP-297, and PPAR agonists such as gemfibrozil, clofibrate, fenofibrate and bezafibrate, and (ii) biguanides, such as metformin and phenformin;

(c) insulin or insulin mimetics;

(d) sulfonylureas and other insulin secretagogues such as tolbutamide, glipizide, meglitinide and related materials;

(e) alpha-glucosidase inhibitors, such as acarbose;

(f) glucagon receptor antagonists such as those disclosed in WO 98/04528, WO 99/01423, WO 00/39088 and WO 00/69810;

(g) GLP-1, GLP-1 analogs, and GLP-1 receptor agonists such as those disclosed in WO0/42026 and WO00/59887;

(h) GIP, GIP mimetics such as those disclosed in WO00/58360, and GIP receptor agonists;

(i) PACAP, PACAP mimetics, and PACAP receptor 3 agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, rosuvastatin, and other statins), (ii) bile-acid sequestrants (cholestyramine, colestipol, and dialkylaminoalkyl derivatives of a cross-linked dextran), (iii) nicotinyl alcohol, nicotinic acid or a salt thereof, (iv) inhibitors of cholesterol absorption, such as ezetimibe and beta-sitosterol, (v) acyl CoA:cholesterol acyltransferase inhibitors, such as, for example, avasimibe, and (vi) anti-oxidants, such as probucol;

(k) PPAR delta agonists, such as those disclosed in WO97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions other than glucocorticoids, such as aspirin, non-steroidal antiinflammatory drugs, azulfidine, and selective cyclooxygenase-2 inhibitors;

(o) protein tyrosine phosphatase 1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan.

The above combinations include a compound of structural formula I, or a pharmaceutically acceptable salt or solvate thereof, with one or more other active compounds. Non-limiting examples include combinations of compounds of structural formula I with two or more active compounds selected from biguanides, sulfonylureas, HMG-CoA reductase inhibitors, PPAR agonists, PTP-1B inhibitors, DP-IV inhibitors, and anti-obesity compounds.

Any suitable route of administration may be employed for providing a mammal, especially a human, with an effective dose of a compound of the present invention. For example, oral, rectal, topical, parenteral, ocular, pulmonary, nasal and the like may be employed. Dosage forms include tablets, troches, dispersions, suspensions, solutions, capsules, creams, ointments, aerosols and the like. Preferably the compound of structural formula I is administered orally.

The effective dosage of the active ingredient varies depending on the particular compound employed, the mode of administration, the condition being treated and the severity of the condition. Such dosages may be ascertained readily by a person skilled in the art. Dosages that are described as "effective amounts" for the treatment of a particular disease or condition may overlap and generally fall within the ranges provided below.

When treating or preventing the diseases and conditions described herein, for which compounds of structural formula I are indicated, satisfactory results are obtained when the compounds of the invention are administered at a daily dosage of from about 0.005 to about 50 milligram per kilogram (mpk) of body weight, preferably given as a single daily dose or in divided doses about two to six times a day. The total daily dosage thus ranges from about 0.3 mg to about 4000 mg, preferably from about 1 mg to about 100 mg. In the case of a typical 70 kg adult human, the total daily dose will range from about 0.3 mg to about 4000 mg. This dosage may be adjusted to provide the optimal therapeutic response.

Dosages for the additional medications described herein in combination with the compounds of formula I include the usual dosages that are prescribed, and may be adjusted by the clinician taking into account the desired result, patient tolerance, side effects and other factors within the clinician's level of skill.

Another aspect of the present invention relates to a pharmaceutical composition which comprises a compound of structural formula I, or a pharmaceutically acceptable salt or solvate thereof, in combination with a pharmaceutically acceptable carrier.

The compositions include compositions suitable for oral, rectal, topical, parenteral (including subcutaneous, intramuscular, and intravenous), ocular (ophthalmic), transdermal, pulmonary (nasal or buccal inhalation), or nasal administration, although the most suitable route in any given case will depend on the nature and severity of the condition being treated and the active ingredient. They may be conveniently presented in unit dosage form and prepared by any of the methods well-known in the art of pharmacy.

The compound of structural formula I can be combined with the pharmaceutical carrier according to conventional pharmaceutical compounding techniques. Carriers take a wide variety of forms. For example, carriers for oral liquid compositions include, e.g., water, glycols, oils, alcohols, flavoring agents, preservatives, coloring agents and other components used in the manufacture of oral liquid suspensions, elixirs and solutions. Carriers such as starches, sugars and microcrystalline cellulose, diluents, granulating agents, lubricants, binders, disintegrating agents and the like are used to prepare oral solid dosage forms, e.g., powders, hard and soft capsules and tablets. Solid oral preparations are preferred over oral liquids.

The oral solid dosage forms may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. Capsules may also contain a liquid carrier such as a fatty oil.

Various other materials may be present to act as coatings or to modify the physical form of the dosage unit. For instance, tablets may be coated with shellac, sugar or both.

Tablets may be coated by standard aqueous or nonaqueous techniques. The typical percentage of active compound in these compositions may, of course, be varied from about 2 percent to about 60 percent on a w/w basis. Thus, tablets contain a compound of structural formula I or a salt or hydrate thereof in an amount ranging from as low as about 0.1 mg to as high as about 1.5 g, preferably from as low as about 1.0 mg to as high as about 500 mg, and more preferably from as low as about 10 mg to as high as about 100 mg.

Oral liquids such as syrups or elixirs may contain, in addition to the active ingredient, sucrose as a sweetening agent, methyl and propylparabens as preservatives, a dye and a flavoring such as cherry or orange flavor.

Parenterals are typically in the form of a solution or suspension, typically prepared with water, and optionally including a surfactant such as hydroxypropylcellulose. Dispersions can be prepared in glycerol, liquid polyethylene glycols and mixtures thereof in oils. Typically preparations that are in diluted form also contain a preservative.

The pharmaceutical injectable dosage forms, including aqueous solutions and dispersions and powders for the extemporaneous preparation of injectable solutions or dispersions, are also sterile and must be fluid to the extent that easy syringability exists; they must be stable under the conditions of manufacture and storage and are usually preserved. The carrier thus includes the solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I of the present invention can be prepared according to the procedures of the following Schemes and Examples.

Abbreviations Used in the Description of the Preparation of the Compounds of the Present Invention:

| AIBN | 2,2'-azobisisobutyronitrile |
|---|---|
| BOC | t-butyloxycarbonyl |
| 9-BBN | 9-borabicyclo[3.3.1]nonane |
| Bn | Benzyl |
| nBuLi | n-butyl lithium |
| Cbz | benzyloxycarbonyl |
| CDI | 1,1'-carbonyldiimidazole |
| MeOTf | methyl trifluoromethanesulfonate |
| (COCl)2 | oxalyl chloride |
| DAST | (diethylamino)sulfur trifluoride |
| DCM | dichloromethane |
| DIEA | diisopropylethylamine |
| DMAP | 4-(dimethylamino)pyridine |
| DMC | 2-chloro-1,3-dimethylimidazolinium chloride |
| DMF | N,N-dimethylformamide |
| Et | Ethyl |
| $Et_3N$ | Triethylamine |
| EtOAc | ethyl acetate |
| EtOH | Ethanol |
| $Et_2Zn$ | Diethylzinc |
| HATU | O-(7-azabenzotriazol)-N,N,N',N'-tetramethyluronium haxafluorophosphate |
| Me | Methyl |
| MeCN | Acetonitrile |
| MeOH | Methanol |
| mCPBA | meta-chloroperbenzoic acid |
| MS | mass spectrum |
| NaOAc | sodium acetate |
| NBS | N-bromosuccinimide |
| Ph | Phenyl |
| PyBROP | bromotripyrrolidinophosphonium hexafluorophosphate |
| $PPh_3$ | triphenylphosphine |
| pyr | Pyridine |
| $SOCl_2$ | thionyl chloride |
| TFA | trifluoroacetic acid |
| TFFH | N,N,N',N'-tetramethylformamidinium hexafluorophosphate |
| THF | tetrahydrofuran |
| TLC | thin-layer chromatography |
| TsOH | p-toluenesulfonic acid |

Example 1

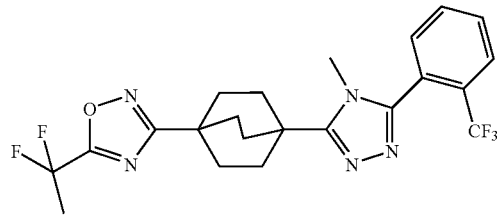

5-(1,1-Difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole (1-H)

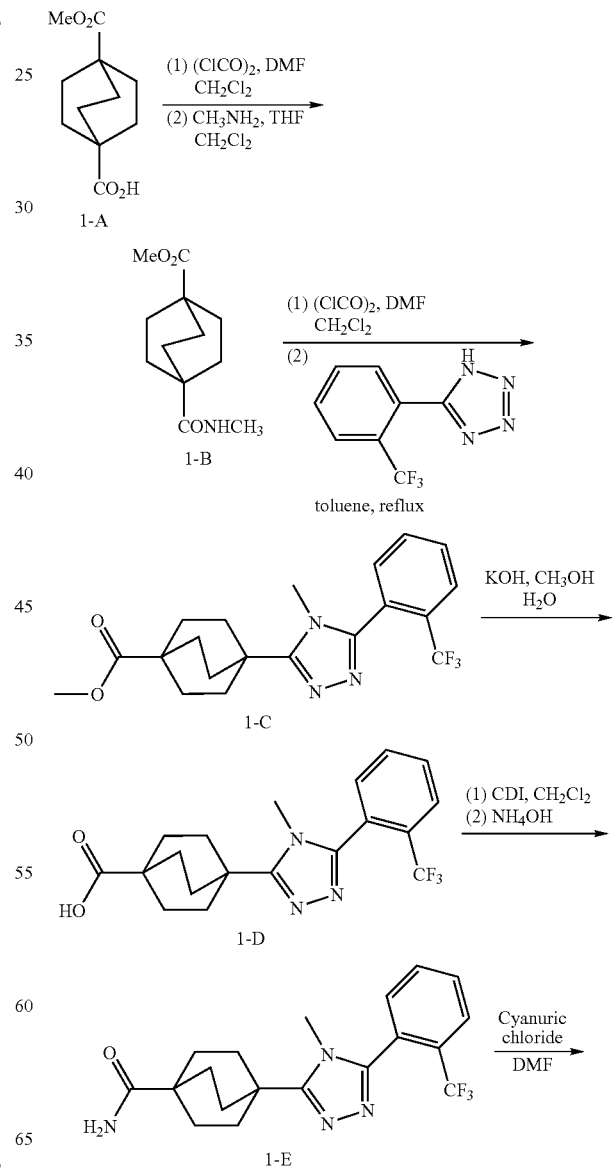

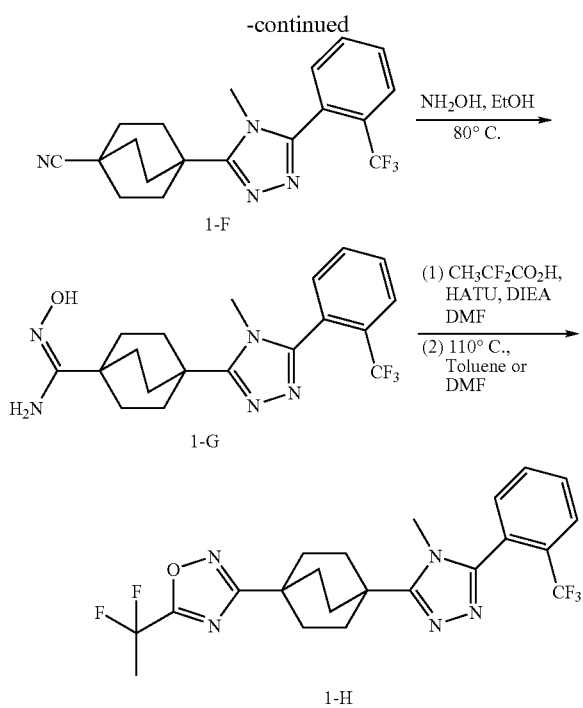

Step A:

4-(Methoxycarbonyl)bicyclo[2.2.2]octane-1-carboxylic acid 1-A (Chapman, N. B. et al. J. Org. Chem., 1970, 35, 917) (4.0 g, 18.9 mmol) was dissolved in 12 mL of anhydrous methylene chloride under nitrogen atmosphere, treated with oxalyl chloride (2M in methylene chloride, 28 mL, 56 mmol) and subsequently with 0.5 ml of DMF. The reaction was stirred at room temperature under nitrogen atmosphere for 90 min, then evaporated and placed under vacuum for 20 min. The acid chloride was dissolved in anhydrous methylene chloride (75 mL), cooled in an ice-bath, and then treated dropwise with a solution of methylamine (2M in THF, 57 mL, 113 mmol). Upon addition of the amine, the cooling bath was removed and the reaction stirred at ambient temperature for 30 min. The mixture was diluted with 1000 mL of methylene chloride and washed with 1N aqueous HCl, saturated aqueous sodium bicarbonate, and brine. The organic layer was dried over anhydrous sodium sulfate and evaporated. Product was purified by flash silica gel chromatography, eluting with 0-5% MeOH/CH$_2$Cl$_2$ gradient to yield methyl 4-[(methylamino)carbonyl]bicyclo[2.2.2]octane-1-carboxylate 1-B as a white solid. MS (ESI$^+$)=226.2 (M+1).

Step B:

Methyl 4-[(methylamino)carbonyl]bicyclo[2.2.2]octane-1-carboxylate 1-B (2.76 g, 12.3 mmol) was dissolved in methylene chloride (100 ml), and oxalyl chloride (2.0 M in DCM, 15.3 ml) was added to the resulting solution followed by DMF (0.19 ml, 2.45 mmol). The reaction mixture was then stirred at room temperature under nitrogen for 2 hours before it was concentrated and stripped with toluene 3 times. The residue was redissolved in toluene (100 ml), treated with 5-[2-(trifluoromethyl)phenyl]-1H-tetrazole (3.15 g, 14.7 mmol) and refluxed under nitrogen for 12 hours. The product, 1,2,4-triazole 1-C, which precipitated out of reaction mixture as the HCl salt, was dissolved in DCM, washed twice with saturated aqueous sodium bicarbonate solution, dried (MgSO$_4$) and stripped to yield a white solid. MS (ESI+)= 394.2 (M+1); $^1$H NMR (500 MHz, CDCl$_3$): δ 2.00 (6H, m), 2.18 (6H, m), 3.48 (3H, s), 3.72 (3H, s), 7.51 (1H, m), 7.71 (2H, m), 7.85 (1H, m) ppm.

Step C:

A solution of methyl ester 1-C (1.19 g, 3.0 mmol) in 5% H$_2$O/MeOH (30 ml) was treated with KOH (0.51 g, 9.0 mmol) at 60° C. under nitrogen atmosphere for 18 h. The resulting mixture was concentrated, diluted with water (150 ml), washed with EtOAc and acidified with aqueous HCl (1N) to pH=3. The precipitate was filtered, washed with a small amount of water and ether and dried under vacuum to yield a pink solid (4-{4-methyl-5-[2-(trifluoromethyl)phenyl]-4H-1,2,4-triazol-3-yl}bicyclo[2.2.2]octane-1-carboxylic acid (1-D)). $^1$H NMR (500 MHz, CD$_3$OD): δ 2.00 (6H, m), 2.17 (6H, m), 3.55 (3H, s), 7.62 (1H, m), 7.85 (2H, m), 7.96 (1H, m) ppm.

Step D:

A portion of solid 4-{4-methyl-5-[2-(trifluoromethyl)phenyl]-4H-1,2,4-triazol-3-yl}bicyclo[2.2.2]octane-1-carboxylic acid (1-D, 0.67 g, 1.77 mmol) was suspended in CH$_2$Cl$_2$ (15 ml) and treated with 1',1'-carbonyldiimidazole (0.57 g, 3.54 mmol) at room temperature under nitrogen atmosphere. After 2 h, concentrated ammonium hydroxide was added (40 ml) and the reaction was stirred for 18 h. The crude mixture was diluted with water (150 ml) and extracted with 3 portions of CH$_2$Cl$_2$ (70 ml). The organic washes were combined, washed with brine, dried over Na$_2$SO$_4$, and the solvent was removed under reduced pressure to yield carboxamide 1-E as a white powder. MS (ESI$^+$)=379.3 (M+1).

Step E:

A solution of carboxamide 1-E (0.64 g, 1.7 mmol) and cyanuric chloride (0.47 g, 2.53 mmol) in DMF (15 ml) was stirred at room temperature under nitrogen atmosphere. After 2 h, DMF was removed in vacuo and the solid was redissolved in CH$_2$Cl$_2$ (100 ml) and washed with saturated aqueous sodium bicarbonate and brine, dried (Na$_2$SO$_4$), and the solvent was removed under reduced pressure to give the nitrile 1-F as a pale yellow solid. MS (ESI$^+$)=361.3 (M+1); $^1$H NMR (500 MHz, CDCl$_3$): δ 2.15 (6H, m), 2.22 (6H, m), 3.47 (3H, s), 7.51 (1H, m), 7.72 (2H, m), 7.87 (1H, m) ppm.

Step F:

A solution of nitrile 1-F (0.56 g, 1.6 mmol) and hydroxylamine (50% aqueous, 4 ml) in ethanol (40 ml) was heated at 80° C. for 18 h. The resulting mixture was cooled to room temperature and concentrated in vacuo. The solid was suspended in toluene, the solvent removed in vacuo, and the solid (1-G) was dried under reduced pressure, and used in the next step without further purification. MS (ESI$^+$)=394.3 (M+1).

Step G:

HATU ((2.93 g, 7.63 mmol) was added to a solution of 2,2-difluoropropinic acid (0.84 g, 7.63 mmol) and N'-hydroxy-4-{4-methyl-5-[2-(trifluoromethyl)phenyl]-4H-1,2,4-triazol-3-yl}bicyclo[2.2.2]octane-1-carboximidamide (1-G) (1.0 g, 2.54 mmol) in anhydrous DMF (30 ml), followed by DIEA (2.2 ml, 12.7 mmol). The resulting mixture was stirred at room temperature for 48 hours, then heated to 110° C. for 3 hours. After cooling to room temperature, the solvent was removed under reduced pressure. The residue was dissolved in ethyl acetate, washed with water, saturated sodium bicarbonate and brine. The crude product was purified by column chromatography with 100% ethyl acetate as eluent to give 1-H as a white powder. MS (ESI$^+$)=468.3 (M+1); $^1$H NMR (500 MHz, CDCl₃): δ 2.10-2.34 (15H, m), 3.57 (3H, s), 7.73-7.75 (3H, m), 7.86 (1H, m) ppm.

Example 2

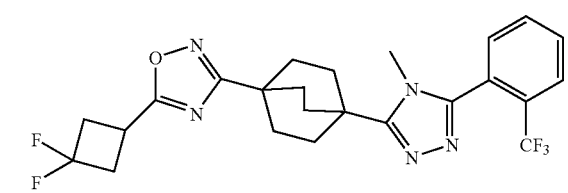

5-(3,3-Difluorocyclobutyl)-3-(4-{4-methyl-5-[2-(trifluoromethyl phenyl]4H-1,2,4-triazol-3-yl}bicyclo[2.2.2]oct-1-yl)-1,2,4-oxadiazole (2-E)

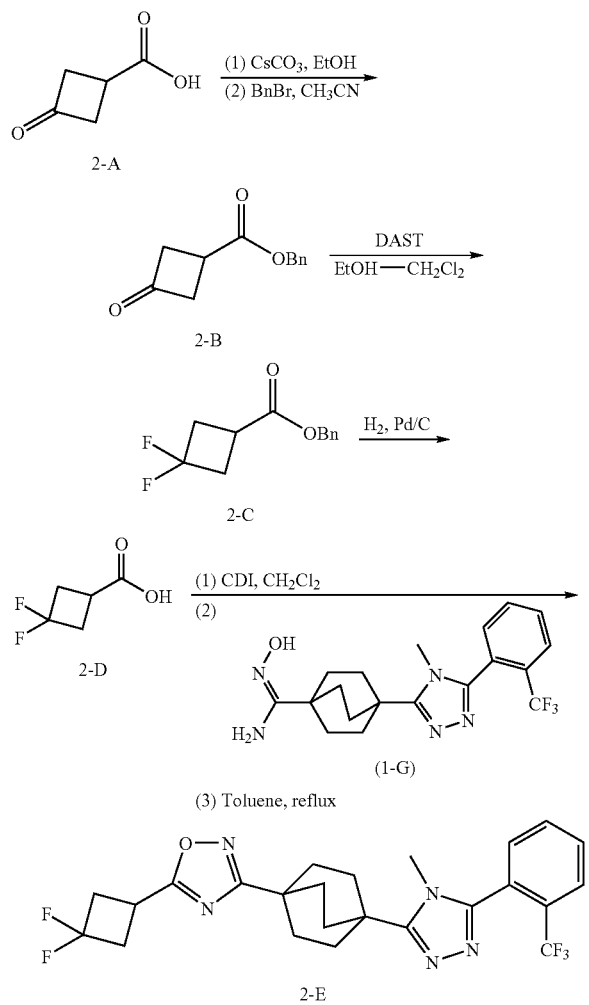

Step A:

3-Oxocyclobutanecarboxylic acid (2-A) (1.0 g, 10.0 mmol) was dissolved in anhydrous ethanol (25 ml), and cesium carbonate (1.66 g, 5.1 mmol) was added. After stirring at room temperature under nitrogen for 4 hours, the reaction mixture was concentrated. The residue was redissolved in anhydrous acetonitrile (50 ml) and treated with benzyl bromide (1.2 ml, 10.0 ml). The mixture was allowed to stir at room temperature under nitrogen for 12 hours. Solvent was then removed under reduced pressure and the residue was partitioned between ethyl acetate and water. The crude product was purified with silica gel chromatography eluting with a gradient of 100% hexane to 96% hexane/ethyl acetate to give 2-B. ¹H NMR (500 MHz, CDCl₃): δ 3.30-3.48 (5H, m), 5.22 (2H, s), 7.37-7.41 (5H, m) ppm.

Step B:

Benzyl 3-oxocyclobutanecarboxylate (2-B) (1.23 g, 6.03 mmol) was dissolved in methylene chloride (35 ml). DAST (8.0 ml, 6.03 mmol) was added under nitrogen, followed by anhydrous ethanol (0.4 ml, 7.23 mmol). The mixture was stirred for 12 hours before it was diluted with methylene chloride, washed successively with saturated sodium bicarbonate, 1N aq. hydrochloric acid, and brine. The organic layer was dried over anhydrous sodium sulfate, filtered and concentrated. The crude product was purified by silica gel chromatography with 93% hexane/ethyl acetate as eluent to give 2-C as an oil. ¹H NMR (500 MHz, CDCl₃): δ 2.81-2.93 (4H, m), 3.01-3.04 (1H, m), 5.20 (2H, s), 7.36-7.42 (5H, m) ppm.

Step C:

Benzyl 3,3-difluorocyclobutanecarboxylate (2-C) (0.84 g, 3.72 mmol) was dissolved in ethanol (40 ml), and approximately 20 mg of palladium on activated carbon was added. The mixture was stirred at room temperature under hydrogen atmosphere for 12 hours, and then filtered through a pad of Celite. The filtrates were concentrated and dried in vacuo to give 2-D. ¹H NMR (500 MHz, CDCl₃): δ 2.86-2.93 (4H, m), 3.02-3.04 (1H, m) ppm.

Step D:

N'-Hydroxy-4-{4-methyl-5-[2-(trifluoromethyl)phenyl]-4H-1,2,4-triazol-3-yl}bicyclo[2.2.2]octane-1-carboximidamide (1-G) (120 mg, 0.305 mmol) was added to a pre-stirred solution of 3,3-difluorocyclobutanecarboxylic acid 2-D (166 mg, 1.22 mmol) and carbonyldiimidazole (198 mg, 1.22 mmol) in CH₂Cl₂ (8 ml). The resulting mixture was stirred at room temperature for 48 h, then concentrated. The solid was resuspended in toluene and refluxed under nitrogen atmosphere for 3 h. The product was purified by C-18 reverse phase HPLC eluting with 30-80% acetonitrile/water with 0.1% TFA to yield 2-E as a white powder. MS (ESI⁺)=494.2 (M+1); ¹H NMR (500 MHz, CDCl₃): δ 2.09 (6H, m), 2.31 (6H, m), 3.03-3.11 (4H, m), 3.57-3.61 (4H, m), 7.56 (1H, m), 7.71 (2H, m), 7.86 (1H, m) ppm Example 3

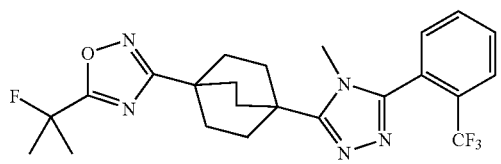

5-(1-Fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole (3-A)

2-(1,1-Difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole (4-B)

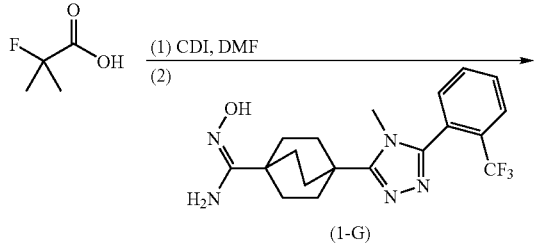

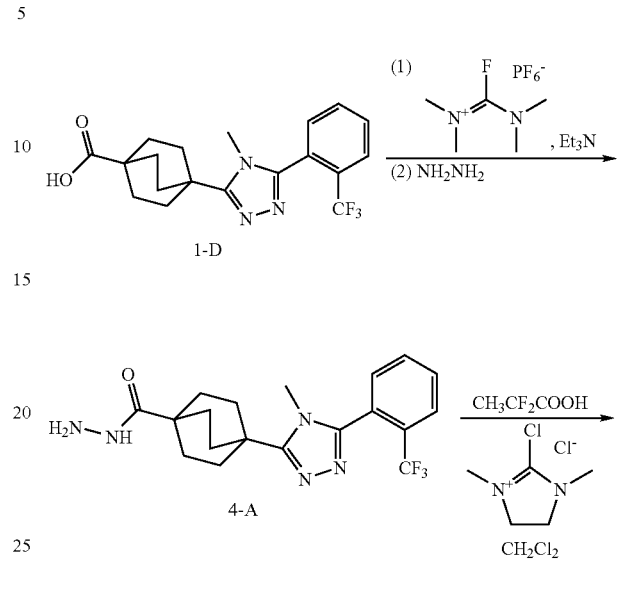

A solution of 2-methyl-2-fluoropropionic acid (108 mg, 1.02 mmol) and 1'1'-carbonyldiimidazole (144 mg, 0.888 mmol) in anhydrous DMF (2.5 ml) was stirred at room temperature under nitrogen atmosphere for 30 min. To this was added N'-Hydroxy-4-{4-methyl-5-[2-(trifluoromethyl)phenyl]-4H-1,2,4-triazol-3-yl}bicyclo[2.2.2]octane-1-carboximidamide (1-G) (139.5 mg, 0.355 mmol) and the solution stirred overnight under $N_2$. The reaction was heated for 1.5 hr at 100° C. in a heat block. DMF was removed in vacuo and the solid was redissolved in $CH_3CN$ (4 ml). The product was purified by C-18 reverse phase chromatography eluting with 10-90% $CH_3CN$ (0.1% TFA)/water (0.1% TFA). The solvent was removed and the residue taken up in DCM and free-based from saturated aqueous sodium bicarbonate solution. The organic layers were dried over $MgSO_4$ and filtered. The solvent was replaced with $CH_3CN$/water and lyophilized to afford 5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole (3-A) as a white solid. MS (ESI$^+$)= 464.13 (M+1). $^1$H NMR (500 MHz, CDCl$_3$): δ 7.89-7.85 (m, 1H), 7.75-7.69 (m, 2H), 7.55 (t, 1H), 3.52 (s, 3H), 2.30 (dd, 6H), 2.15 (dd, 6H), 1.90 (s, 3H), 1.86 (s, 3H).

Example 4

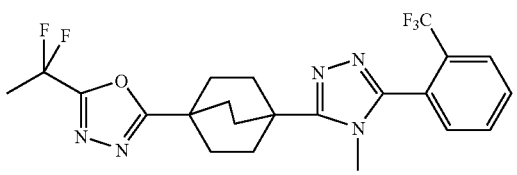

Step A:

Acid 1-D (1.0 g, 2.64 mmol) was dissolved in DMF (30 ml), and TFFH (0.84 g, 3.18 mmol) was added followed by triethylamine (0.88 ml, 6.34 mmol) and anhydrous hydrazine (0.12 ml, 3.95 mmol). The mixture was stirred at room temperature under nitrogen for 12 hours. The mixture was then concentrated under reduced pressure to remove DMF. The residue was taken up in ethyl acetate and washed with saturated sodium bicarbonate and brine. The organic layer was dried over anhydrous sodium sulfate, filtered and concentrated. The product (4-{4-methyl-5-[2-(trifluoromethyl)phenyl]-4H-1,2,4-triazol-3-yl}bicyclo[2.2.2]octane-1-carbohydrazide, 4-A) was further dried by co-evaporating with toluene several times before being used in the next step.

MS (ESI$^+$)=394.2 (M+1).

Step B:

A mixture of 4-{4-methyl-5-[2-(trifluoromethyl)phenyl]-4H-1,2,4-triazol-3-yl}bicyclo[2.2.2]octane-1-carbohydrazide (4-A) (334 mg, 0.850 mmol) and 2,2-difluoropropionic acid (78 mg, 0.708 mmol) was suspended in methylene chloride, and DMC (1.2 g, 7.08 mmol) was added as solid. The mixture was stirred at room temperature under nitrogen for 48 hours before it was diluted with methylene chloride, washed with water, saturated sodium bicarbonate and brine. The crude product was purified by column chromatography to give 4-B as a white solid. MS (ESI$^+$)=468.3 (M+1); $^1$H NMR (500 MHz, CDCl₃): δ 2.15-2.33 (15H, m), 3.52 (3H, s), 7.61 (1H, m), 7.72 (2H, m), 7.85 (1H, m) ppm.

Example 5

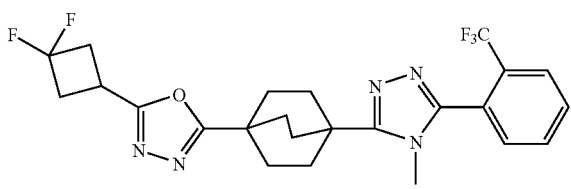

2-(3,3-Difluorocyclobutyl)-5-(4-{4-methyl-5-[2-(trifluoromethyl)phenyl]-4H-1,2,4-triazol-3-yl}bicyclo[2.2.2]oct-1-y)-1,3,4-oxadiazole (5-A)

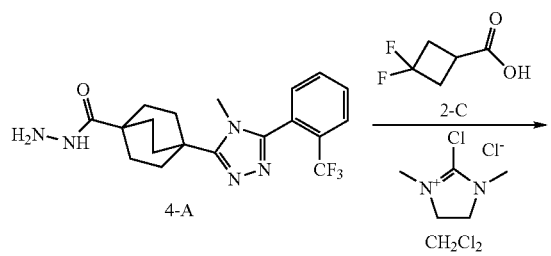

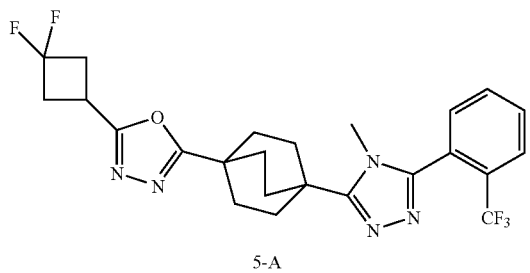

Step A:

Triazole 5-A was prepared from hydrazide 4-A (119 mg, 0.303 mmol) and 3,3-difluorocyclobutanecarboxylic acid (49.4 mg, 0.363 mmol) using the method described in Example 4, step B. 2-(3,3-Difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole (5-A) was isolated as a white powder after purification by C-18 reverse phase HPLC two times (eluting with 20-80% and 25-50% acetonitrile/water, respectively, with 0.1% TFA). MS (ESI⁺)= 494.2 (M+1).

Example 6

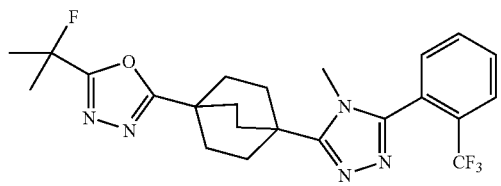

2-(1-Fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole (6-B)

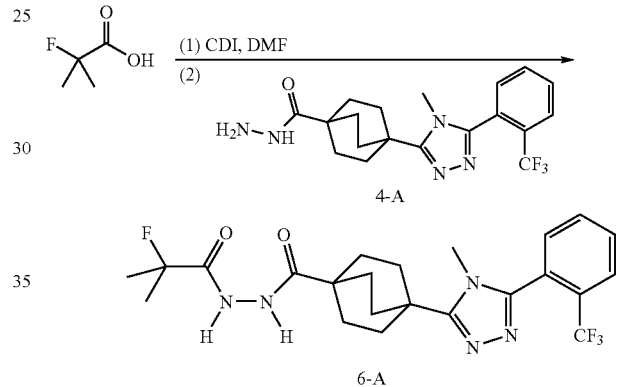

Step A:

A solution of 2-methyl-2-fluoropropionic acid (70 mg, 0.66 mmol) and 1'1'-carbonyldiimidazole (107 mg, 0.66 mmol) in anhydrous DMF (2 ml) was stirred at room temperature under nitrogen atmosphere for 30 min. To this solution was added hydrazide 4-A (200 mg, 0.509 mmol) and the solution was stirred overnight under N₂. DMF was removed in vacuo and the solid was redissolved in CH₃CN (4 ml) with some DMSO. Product was purified by C-18 reverse phase chromatography eluting with 10-90% CH₃CN (0.1% TFA)/water (0.1% TFA). Solvent was removed in vacuo and the product was free-based from DCM and saturated aqueous sodium bicarbonate. The organic layer was dried over MgSO₄ and filtered. The solvent was removed to afford product 6-A. MS (ESI⁺)=482.30 (M+1).

Step B:

To the material obtained in Step A was added toluene (3 mL) and thionyl chloride (2 mL) and, fitted with a reflux condenser, the solution was heated to 85° C. under nitrogen. After 1 hour the solvent was removed under reduced pressure and the residue was dissolved in toluene which was removed under reduced pressure. The residue was dissolved in $CH_3CN$ (4 ml) and the product was purified by C-18 reverse phase chromatography eluting with 10-90% $CH_3CN$ (0.1% TFA)/water (0.1% TFA). Solvent was removed in vacuo and the product was free-based from DCM and saturated aqueous sodium bicarbonate. The organic layer was washed with brine and dried over $MgSO_4$ and filtered. The solvent was removed and the product lyopholyzed from $CH_3CN$ and water to afford 2-(1-fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole (6-B) as a white solid. MS (ESI$^+$)= 463.98 (M+); $^1$H NMR (500 MHz, CDCl$_3$): δ 7.89-7.85 (m, 1H), 7.76-7.70 (m, 2H), 7.58 (s, 1H), 3.53 (s, 3H), 2.32 (dd, 6H), 2.20 (dd, 6H), 1.92 (s, 3H), 1.87 (s, 3H).

Example of a Pharmaceutical Formulation

As a specific embodiment of an oral composition of a compound of the present invention, 50 mg of any of Examples 1-15 is formulated with sufficient finely divided lactose to provide a total amount of 580 to 590 mg to fill a size O hard gelatin capsule.

Assays: Measurement of Inhibition Constants:

In vitro enzymatic activity was assessed for test compounds via a Scintillation Proximity Assay (SPA). In short, tritiated-cortisone substrate, NADPH cofactor and titrated compound of structural formula I were incubated with 11β-HSD1 enzyme at 37° C. to allow conversion to cortisol to progress. Following this incubation, a preparation of protein A coated SPA beads, pre-blended with anti-cortisol monoclonal antibody and a non-specific 11β-HSD inhibitor, such as 18β-glycyrrhetinic acid, was added to each well. The mixture was shaken at 15° C. and was then read on a liquid scintillation counter suitable for 96 well plates. Percent inhibition was calculated relative to a non-inhibited control well and IC$_{50}$ curves were generated. This assay was similarly applied to 11β-HSD2, whereby tritiated cortisol and NAD were used as the substrate and cofactor, respectively. To begin the assay, 40 μL of substrate (25 nM $^3$H-Cortisone+1.25 mM NADPH in 50 mM HEPES Buffer, pH 7.4) was added to designated wells on a 96-well plate. The compound was dissolved in DMSO at 10 mM followed by a subsequent 50 fold dilution in DMSO. The diluted material was then titrated 4 fold, seven times. 1 μL of each titrated compound was then added in duplicate to the substrate. To start the reaction, 10 μL of 11β-HSD1 microsome from CHO transfectants was added to each well at the appropriate concentration to yield approximately 10% conversion of the starting material. For ultimate calculation of percent inhibition, a series of wells were added that represented the assay minimum and maximum: one set that contained substrate without compound or enzyme (background), and another set that contained substrate and enzyme without any compound (maximum signal). The plates were spun briefly at a low speed in a centrifuge to pool the reagents, sealed with an adhesive strip, mixed gently, and incubated at 37° C. for 2 h. After incubation, 45 μL of SPA beads, presuspended with anti-cortisol monoclonal antibody and a compound of formula I, were added to each well. The plates were resealed and shaken gently for greater than 1.5 h at 15° C. Data were collected on a plate based liquid scintillation counter such as a Topcount. To control for inhibition of anti-cortisol antibody/cortisol binding, substrate spiked with 1.25 nM $^3$H cortisol was added to designated single wells. 1 μL of 200 μM compound was added to each of these wells, along with 10 μL of buffer instead of enzyme. Any calculated inhibition was due to compound interfering with the cortisol binding to the antibody on the SPA beads. Using human 11β HSD-1 enzyme, the compounds of the invention demonstrate an IC$_{50}$ value in the range of about 9 nM to about 100 nM. In contrast, the range of demonstrated activity for 11β HSD-2 is from about 1.7 micromolar to greater than 4 micromolar.

Assays: Measurement of In Vivo Inhibition:

In general terms, the test compound was dosed orally to mice and a prescribed time interval was allowed to elapse, usually between 1 and 24 h. Tritiated cortisone was injected intravenously, followed several min later by blood collection. Steroids were extracted from the separated serum and analyzed by HPLC. The relative levels of $^3$H-cortisone and its reduction product, $^3$H-cortisol, were determined for the compound and vehicle-dosed control groups. The absolute conversion, as well as the percentage of inhibition, was calculated from these values.

More specifically, compounds were prepared for oral dosing by dissolving them in vehicle (5% hydroxypropyl-beta-cyclodextrin v/v $H_2O$, or equivalent) at the desired concentration to allow dosing at typically 10 mg per kg. Following an overnight fasting, the solutions were dosed to ICR mice (obtained from Charles River) by oral gavage, 0.5 mL per dose per animal, with three animals per test group.

After the desired time had passed, routinely either 4 or 16 h, 0.2 mL of 3 μM $^3$H-cortisone in dPBS was injected by tail vein. The animal was caged for two min followed by euthanasia in a $CO_2$ chamber. Upon expiration, the mouse was removed and blood was collected by cardiac puncture. The blood was set aside in a serum separation tube for no less than 30 min at room temperature to allow for adequate coagulation. After the incubation period, blood was separated into serum by centrifugation at 3000×g, 4° C., for 10 min.

To analyze the steroids in the serum, they were first extracted with organic solvent. A 0.2 mL volume of serum was transferred to a clean microcentrifuge tube. To this a 1.0 mL volume of ethyl acetate was added, followed by vigorous vortexing for 1 min. A quick spin on a microcentrifuge pelleted the aqueous serum proteins and clarified the organic supernatant. 0.85 mL of the upper organic phase was transferred to a fresh microcentrifuge tube and dried. The dried sample was resuspended in 0.250 mL of DMSO containing a high concentration of cortisone and cortisol for analysis by HPLC.

A 0.200 mL sample was injected onto a Metachem Inertsil C-18 chromatography column equilibrated in 30% methanol. A slow linear gradient to 50% methanol separated the target steroids; simultaneous monitoring by UV at 254 nm of the cold standards in the resuspension solution acted as an internal standard. The tritium signal was collected by a radiochromatography detector that uploaded data to software for analysis. The percent conversion of $^3$H-cortisone to $^3$H-cortisol was calculated as the ratio of AUC for cortisol over the combined AUC for cortisone and cortisol. The percent of inhibition of conversion of tritiated cortisone to tritiated cortisol was in the range of about 86 to 98%.

While the invention has been described and illustrated in reference to specific embodiments thereof, those skilled in the art will appreciate that various changes, modifications, and substitutions can be made therein without departing from the spirit and scope of the invention. Consequently, the claims are not to be limited thereby.

What is claimed is:

1. A compound represented by formula I:

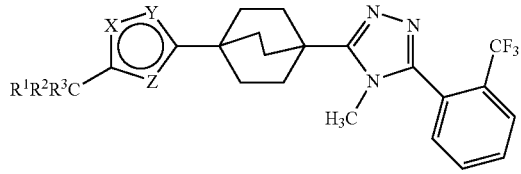

or a pharmaceutically acceptable salt thereof wherein:
2 of X, Y and Z represent nitrogen atoms, and the other represents an oxygen atom;
R¹ and R² are taken together with the atom to which they are attached and represent a cyclobutyl group, optionally substituted with 1-2 fluorine atoms, and R³ represents hydrogen or a fluorine atom;
or R¹ represents methyl,
R² represents methyl or a fluorine atom and
R³ represents a fluorine atom.

2. A compound in accordance with claim 1 selected from the group consisting of:

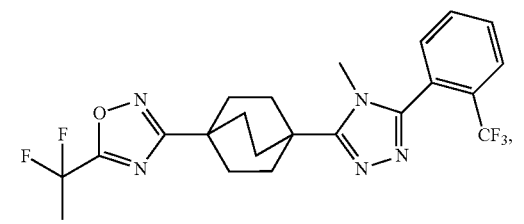

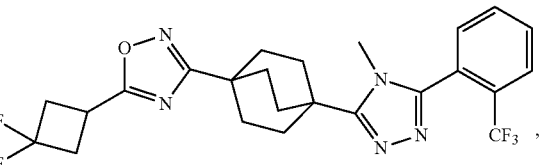

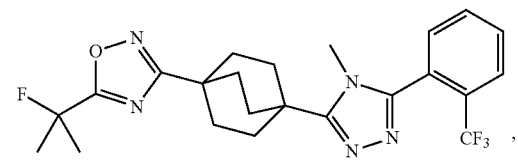

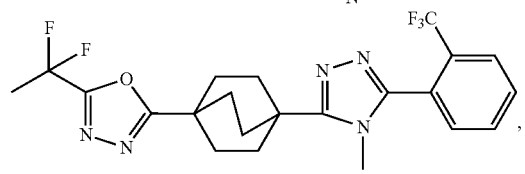

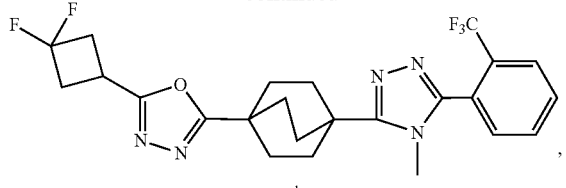

and

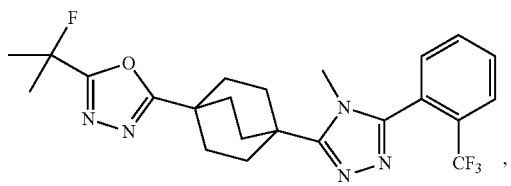

or a pharmaceutically acceptable salt thereof.

3. A pharmaceutical composition comprised of a compound in accordance with claim 1 in combination with a pharmaceutically acceptable carrier.

4. A method of treating hypertension in a mammalian patient in need of such treatment comprising administered to the patient an anti-hypertensive effective amount of a compound in accordance with claim 1.

5. A method of treating diabetes in a mammalian patient in need of such treatment comprising administering to the patient a compound in accordance with claim 1 in an amount that is effective to treat diabetes.

6. A method of treating obesity in a mammalian patient in need of such treatment comprising administering to the patient a compound in accordance with claim 1 in an amount that is effective to treat obesity.

7. A compound which is: 5-(1,1-Difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; or a pharmaceutically acceptable salt thereof.

8. A compound which is: 5-(3,3-Difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole; or a pharmaceutically acceptable salt thereof.

9. A compound which is: 5-(1-Fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; or a pharmaceutically acceptable salt thereof.

10. A compound which is: 2-(1,1-Difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole; or a pharmaceutically acceptable salt thereof.

* * * * *